US008996314B2

(12) United States Patent
Ohnemus et al.

(10) Patent No.: US 8,996,314 B2
(45) Date of Patent: Mar. 31, 2015

(54) SYSTEM AND METHOD FOR PERSONAL STRESS ANALYSIS

(75) Inventors: Peter Ohnemus, Küsnacht (CH); Laurence Jacobs, Thalwil (CH); Andre Naef, Zurich (CH)

(73) Assignee: Dacadoo AG, Zurich (CH)

( * ) Notice: Subject to any disclaimer, the term of this patent is extended or adjusted under 35 U.S.C. 154(b) by 311 days.

(21) Appl. No.: 13/542,542

(22) Filed: Jul. 5, 2012

(65) Prior Publication Data
US 2013/0013208 A1 Jan. 10, 2013

Related U.S. Application Data

(63) Continuation of application No. PCT/EP2012/062948, filed on Jul. 3, 2012.

(60) Provisional application No. 61/505,087, filed on Jul. 6, 2011.

(51) Int. Cl.
G06F 19/00 (2011.01)
(52) U.S. Cl.
CPC ............... *G06F 19/3431* (2013.01)
USPC ........................................................... 702/3
(58) Field of Classification Search
CPC ......... A61B 5/486; A61B 5/16; A61B 5/7264
USPC ............................................. 702/3, 182–185
See application file for complete search history.

(56) References Cited

U.S. PATENT DOCUMENTS

| 6,454,705 | B1 | 9/2002 | Cosentino et al. |
| 7,024,370 | B2 | 4/2006 | Epler et al. |
| 7,904,310 | B2 | 3/2011 | Brown |
| 2004/0172290 | A1 | 9/2004 | Leven |
| 2007/0027367 | A1 | 2/2007 | Oliver et al. |
| 2008/0146892 | A1 | 6/2008 | LeBoeuf et al. |
| 2009/0163774 | A1 | 6/2009 | Thatha et al. |
| 2010/0160743 | A1 | 6/2010 | Jeong et al. |
| 2010/0324427 | A1* | 12/2010 | Devot et al. .................. 600/484 |
| 2011/0288379 | A1 | 11/2011 | Wu |

FOREIGN PATENT DOCUMENTS

| WO | WO 2004/032715 | 4/2004 |
| WO | WO 2007/112034 | 10/2007 |
| WO | WO 2012/050969 | 4/2012 |

OTHER PUBLICATIONS

International Search Report and Written Opinion dated Oct. 27, 2014 for PCT/ib2013/003171.

* cited by examiner

*Primary Examiner* — Edward Raymond
(74) *Attorney, Agent, or Firm* — Leason Ellis LLP

(57) ABSTRACT

There is shown and described a computer implemented system and method for analyzing an individual's personal stress level and providing a stress-score representing the individual's personal stress level. A plurality of parameters are received into a memory from at least one computing device and each of the parameters respectively represents a factor of the individual's life that contributes to a level of stress for the individual. The received parameter data is processed by executing code in a processor that configures the processor to normalize the parameter data by assigning, for each of the received parameters, a respective parameter score that represents a relative value of the parameter. The individual's stress-score is calculated as a function of the normalized parameter data, the stress-score is automatically transmitted to the at least one computing device, using code executing in the processor and free of human intervention.

38 Claims, 3 Drawing Sheets

SYSTEM AND METHOD FOR PERSONAL STRESS ANALYSIS

CROSS REFERENCE TO RELATED APPLICATIONS

The present application is a continuation of International PCT Patent Application No. PCT/EP2012/062948, filed Jul. 3, 2012, which claims the benefit of U.S. Patent Application Ser. No. 61/505,087, filed Jul. 6, 2011, which are hereby incorporated by reference in their entirety.

FIELD OF THE INVENTION

The present invention concerns a device for tracking the activities of a person to calculate a level of chronic stress of the person. More particularly, the invention concerns a device that collects information about a person's biometrics activities and environmental conditions to calculate a stress-score indicative of the user's level of chronic stress.

BACKGROUND OF THE INVENTION

People experience high levels of stress in their life, much of which is attributable to work commitments. People receive, read, and answer vast numbers of e-mails, engage in telephone conferences, travel to meetings, and are exposed to environmental conditions such as noise and adverse weather, for example. These activities and stimuli may increase the level of stress that a person experiences. When a person experiences high levels of stress there is a risk that he or she will experience a "burn out" and no longer be able to effectively handle his or her responsibilities, which adversely affects a person's ability to continue working. However, a person experiences stress from so many different sources (e.g., e-mail, travel commitments, etc.), it is difficult to quantify a person's stress level before he or she reaches the burn out stage. Moreover, chronic stress has been found to contribute to several major diseases, including clinical depression, cardiovascular and cerebrovascular diseases, HIV, and cancers.

The present invention addresses these and other concerns.

SUMMARY OF THE INVENTION

According to an aspect of the present invention, there is provided a computer implemented method for analyzing an individual's personal stress level and providing a stress-score representing the individual's personal stress level. The method comprises receiving into a memory from at least one computing device parameter data representing a plurality of parameters. Each of the parameters respectively represents a factor of the individual's life that contributes to a level of stress for the individual. The received parameter data is processed by executing code in a processor that configures the processor to normalize the parameter data by assigning, for each of the received parameters, a respective parameter score that represents a relative value of the parameter. The individual's stress-score is calculated as a function of the normalized parameter data, and the stress-score is automatically transmitted to the at least one computing device, using code executing in the processor and free of human intervention.

According to a further aspect of such a method as can be implemented in a particular embodiment thereof, the normalizing the parameters comprises executing code in the processor that configures the processor to determine, for each of the received parameters, an upper bound parameter value and a lower bound parameter value.

According to still another aspect of such a method as can be implemented in a particular embodiment thereof, code is executed in the processor that configures the processor to normalize the parameter data by assigning, for each of the received parameters, a respective parameter score that is within the respective parameter's upper bound parameter value and the lower parameter bound value. In yet another aspect, the calculating the individual's stress-score includes averaging the normalized parameter data.

According to an additional aspect of the present invention, there is provided a computer implemented stress-score calculating system. The system comprises a communication unit operable to receive, from at least one computing device, parameter data representing a plurality of parameters, each of the parameters respectively representing a factor of an individual's life that contributes to a level of stress for the individual. The system further includes a memory arranged to store the received parameter data. The system further includes a processor that is arranged to process the received parameter data by executing code that configures the processor to normalize the parameter data by assigning, for each of the received parameters, a respective parameter score that represents a relative value of the parameter. The processor is further arranged to execute code to calculate the individual's stress-score as a function of the normalized parameter data and to automatically transmit the stress-score to the at least one computing device.

According to a further aspect of such a system as can be arranged in a particular embodiment thereof; the processor is further arranged to normalize the parameters by executing code in the processor that configures the processor to determine, for each of the received parameters, an upper bound parameter value and a lower bound parameter value.

According to still another aspect of such a system as can be arranged in a particular embodiment thereof, the processor is further arranged to assign, for each of the received parameters, a respective parameter score that is within the respective parameter's upper bound parameter value and the lower bound parameter value. Moreover, the processor may be further arranged to calculate the individual's stress-score by averaging the normalized parameter data.

In at least one aspect of the present invention, the plurality of parameters include at least two selected from a group consisting of: an e-mail correspondence parameter, a telephone correspondence parameter, a travel parameter, a task parameter, an appointment parameter, a meeting parameter, a time at work parameter, an ambient noise parameter, a weather parameter, a sleeping habits parameter, an eating habits parameter and a health-related information parameter. The e-mail correspondence parameter may represent at least one selected from a group consisting of: amount of e-mail received, amount of e-mail viewed, an amount e-mail sent, the length of an e-mail message, amount of time spent working with e-mail, and a time of day working with e-mail. Moreover, the telephone correspondence parameter may represent at least one selected from a group consisting of: the number of telephone calls made, the number of telephone calls received, a duration of a telephone call, a time of day of a telephone call, the individual's tone of voice during a telephone call, and the individual's voice pattern during a telephone call.

Furthermore, the travel parameter may represent at least one selected from a group consisting of a location, a time of year, and an amount of travel. The tasks parameter may represent at least one selected from a group consisting of a type of task, a quantity of tasks, and a time of day for performing a task. The appointments parameter may represent at least one selected from a group consisting of a type of appointment, a quantity of appointments, and a time of day for an appointment. The meeting parameter may represent at least one selected from a group consisting of a type of meeting, a count of meetings, and a time of day for a meeting. Furthermore, at least one of the travel parameter, task parameter, appointment parameter and the meeting parameter are determined as a function of Global Positioning System technology. At least one of the e-mail correspondence parameter, the telephone correspondence parameter, the travel parameter, the task parameter, the appointment parameter, the meeting parameter, the time at work parameter, the ambient noise parameter, and the weather parameter may be received as a function of a software application executed on the at least one computing device.

Moreover, a report may be generated and distributed that includes the stress-score.

In at least one aspect of the present invention, code is executed in a processor that configures the processor to generate and transmit a message to at least one other computing device, wherein the message is generated and transmitted based on at least the stress-score. The message may inform the respective user of the at least one other computing device that the individual is temporarily unavailable. Further the message may be generated as a function of at least one rule defined by the individual. In at least one aspect of the present invention, the at least one rule relates to at least one of a sender of an e-mail and a subject line of an e-mail message.

Further, in at least one aspect of the present invention, code is executed in a processor that configures the processor to receive information associated with at least one protocol used in the determination of the stress-score.

In yet another aspect of the present invention, a computer implemented method is provided for collecting information associated with an individual's personal stress level and receiving a stress-score representing the individual's personal stress level. In accordance with such an aspect, parameter data representing a plurality of parameters are obtained, each of the parameters respectively representing a factor of the individual's life that contributes to a level of stress for the individual, wherein the plurality of parameters include at least two selected from a group consisting of: an e-mail correspondence parameter, a telephone correspondence parameter, a travel parameter, a task parameter, an appointment parameter, a meeting parameter, a time at work parameter, an ambient noise parameter, a weather parameter, a sleeping habits parameter, an eating habits parameter and a health-related information parameter. The parameter data are transmitted to at least one computing device, and the stress-score is received from the at least one computing device.

In yet another aspect of the present invention, a computer implemented system is provided for collecting information associated with an individual's personal stress level and receiving a stress-score representing the individual's personal stress level. In accordance with such an aspect, parameter data representing a plurality of parameters are obtained, each of the parameters respectively representing a factor of the individual's life that contributes to a level of stress for the individual, wherein the plurality of parameters include at least two selected from a group consisting of: an e-mail correspondence parameter, a telephone correspondence parameter, a travel parameter, a task parameter, an appointment parameter, a meeting parameter, a time at work parameter, an ambient noise parameter, a weather parameter, a sleeping habits parameter, an eating habits parameter and a health-related information parameter. The parameter data are transmitted to at least one computing device, and the stress-score is received from the at least one computing device.

Other features and advantages of the present application are shown with reference to the accompanying drawing figures, by way of example only, and described below.

DESCRIPTION OF THE DRAWING FIGURES

DETAILED DESCRIPTION OF CERTAIN EMBODIMENTS OF THE INVENTION

The following detailed description, which references to and incorporates the drawings, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1A:
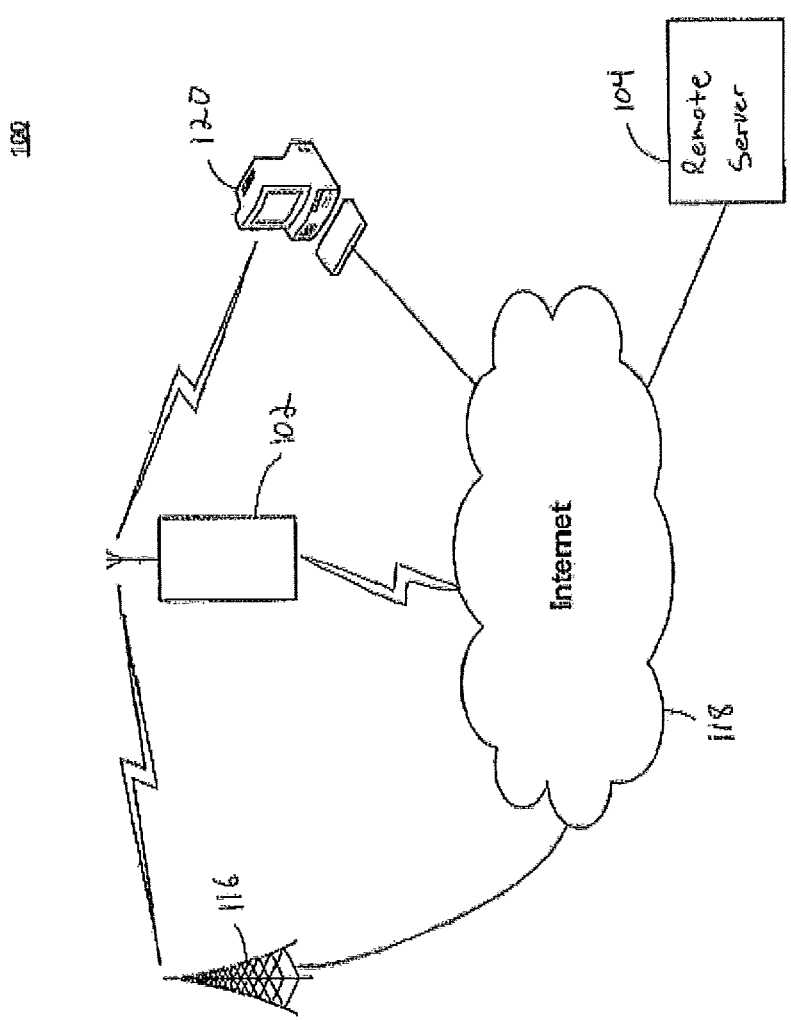
FIG. 1A illustrates an exemplary diagram of a mobile electronic device in wireless communication.
Figure 1B:
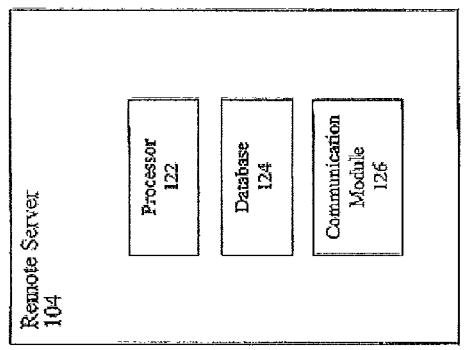
FIG. 1B is a block diagram illustrating certain components of the mobile electronic device and a remote server.
Figure 1B:
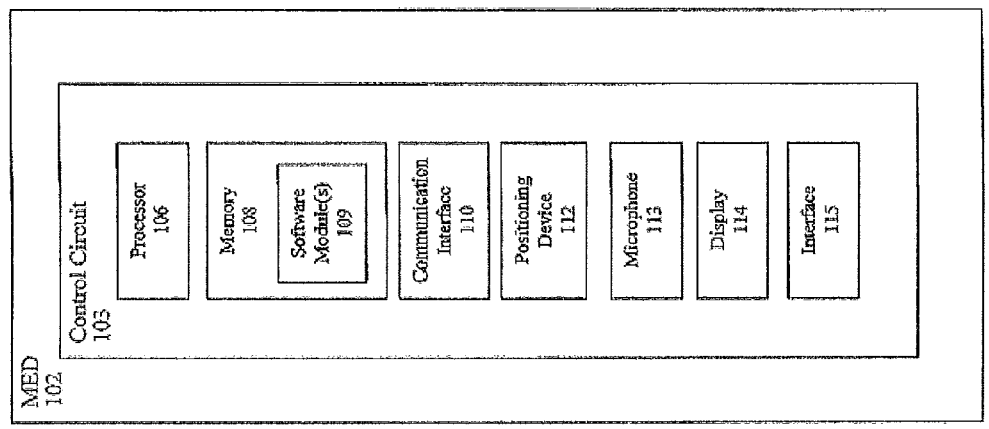

In at least one implementation, and with reference to FIGS. 1A and 1B, a system 100 for determining the stress level of a person includes a mobile electronic device 102 and, optionally, a remote server 104.

The mobile electronic device 102 may be a cell phone, personal digital assistant, smart phone, tablet computing device, or other portable electronic device. Mobile electronic device 102 includes a control circuit 103 which may be operatively connected to various hardware and software components that serve to enable determination of a stress level of a person, as discussed in greater detail below. The control circuit 103 may be operatively connected to a processor 106 and a memory 108. Preferably, memory 108 is accessible by processor 106, thereby enabling processor 106 to receive and execute instructions stored on memory 108.

One or more software modules 109 are encoded in memory 108. The software modules 109 may comprise a software program or set of instructions executed in processor 106. Preferably, the software modules 109 make up a stress monitoring application that collects data that may be used to calculate a stress-score, and perform other functions, that is executed by processor 106. During execution of the software modules 109, the processor 106 configures the control circuit 103 to gather information about the person's activities and environmental stimuli that may induce stress, and other functions, as discussed in greater detail below. It should be noted that while FIG. 1B depicts memory 108 on control circuit 103, in an alternate arrangement, memory 108 may be practically any storage medium (such as a hard disk drive, flash memory, etc.) that is operatively connected to the control circuit 103, even if not oriented on the control circuit as depicted in FIG. 1B.

An interface 115 may be also operatively connected to control circuit 103. The interface 115 preferably includes one or more input device(s) such as a switch, knob, button(s), key(s), touchscreen, etc. Interface 115 may be operatively connected to the control circuit 103 and serves to facilitate the capture of certain profile information and details about the user (e.g., age, profession, etc.). By way of example, input device of interface 115 may be a touch screen display. Accordingly, the display 114 may be used to display a graphical user interface, which displays various to the user. Touching the touch screen interface 115 at locations corresponding to the display of the graphical user interface allows the person to interact with the device to enter data, change settings, control functions, etc. So, when the touch screen is touched, interface 115 communicates this change to control circuit 103, and settings may be changed or user entered information may be captured and stored in the memory 108.

The display 114 includes a screen or any other such presentation device which enables the user to view various options and parameters, and select among them using the interface 115 referenced above. In yet another arrangement, either one or both of the interface 115 and display 114 may be implemented in a non-visual and/or non-tactile fashion, such as by using a series of audio menus and/or voice commands/prompts to select and/or define settings, provide information about the user, and/or control the functions of the system.

A positioning device 112 may be operatively connected to control circuit 103. The positioning device 112 may be a global positioning system (GPS) circuit or a positioning system that relies on triangulation between cell phone towers in order to determine position, or other known position determining means. The positioning device 112 permits the determination of the location of the mobile device 102 and hence the position of the person.

A microphone 113 may be operatively connected to the control circuit 103. The microphone 113 may be a part of the mobile electronic device's telephone communication equipment. The microphone 113 may be used to detect a user's voice during telephone communication. The microphone may also be used to detect volume and other characteristics of a user's voice to detect stress levels and may be used to detect levels of ambient noise.

A communication interface 110 may be operatively connected to control circuit 103. The communication interface 110 may be a cellular communication circuit allowing communication with a cellular network 116, a Wi-Fi communication circuit allowing communication directly to the internet 118 through a Wi-Fi connection, and/or a circuit allowing communication with a computer terminal 120, such as a Bluetooth circuit and/or circuit allowing wired communication. Accordingly, the communication interface 110 allows the mobile electronic device to engage in telephone communications, e-mail communications, text messaging, web surfing, etc. The communication interface may include a number circuits and sub-modules that permit the various means of communication.

Referring to FIG. 1A, an exemplary diagram illustrates the mobile electronic device 102 preferably in wireless communication with communication network 116, such as a cellular communication network. Mobile device 102's communication with communication network 116 facilitates connection to the internet 118. In at least one implementation, a user's stress level is calculated using modules executing on processors at a remote server 104. Remote server 104 may be also connected to the internet 118. Accordingly, the mobile electronic device 102 may communicate with and transmit data to and receive data from the remote server 104 via communication network 116 and the internet 118. The server 104 includes a processor 122, a database 124, and a communication interface 126. However, the use of the remote server 104 to calculate the stress level is optional, and such calculations may be performed using modules executing on the mobile electronic device 102, as described in more detail herein. The mobile electronic device 102 may also communicate a calculated stress-score to the remote server 104 so that the stress-score may be viewed by authorized third parties.

The mobile electronic device 102 may also communicate with a computer terminal 120. Computer terminal 120 may be a personal computer, for example. The mobile electronic device 102 may communicate with the computer terminal 120 via a Wi-Fi or Bluetooth connection, for example. The mobile electronic device 102 may also communicate with the computer terminal 120 via a wired connection, using a USB tether, for example. The computer terminal 120 may be connected to the internet 118. Thus, the mobile electronic device 102 may communicate with the remote server 104 via a computer terminal 120. The mobile electronic device 102 may also communicate with the internet 118 through its communication interface 110 (e.g., Wi-Fi) and thus connect to the remote server 104.

The operation of the mobile device 102 and the various elements described above will be appreciated with reference to the method for calculating the stress level of a person, as described below, in conjunction with FIG. 2.

The system 100 determines the relative stress that a user is experiencing as a result of the values of various parameters. The parameters may include e-mail usage, phone usage, travel, tasks, appointments, meetings, amount of time at work, ambient noise levels, local weather, and other parameters. This is a non-limiting list and other parameters that indicate the stress of a user may also be included. For example, the user may also enter information about sleep habits, eating habits, exercise habits, health conditions, and other parameters that may also be used to determine a user's stress levels.

In at least one implementation, the system 100 includes a data collection module operating on a user mobile electronic device 102 that collects information about a user's activities. The data collection module may be one of the software modules 109 that may be installed on mobile electronic device 102. The mobile electronic device 102 includes a number of other software modules or applications that may be used for e-mail, task management, scheduling, phone calls, to determine the location of a user, etc. The data collection module may be a daemon program that runs under the application layer to track e-mails and phone calls being sent and receive, etc. The data collection module may also be installed and operated as an add-on to the already existing applications running on the device, which will allow additional information to be collected about the activities of the user.

The data collection module collects data concerning a user's e-mail usage. These data may include the number of e-mails received, the number of e-mails viewed, the number of e-mails sent, the length of each e-mail received or sent, the time at which the person is viewing and sending e-mails (indicating the number of hours a day a user is actively managing their e-mails), etc. The more e-mails a person receives, views, and sends, the longer the e-mails, and the greater amount of time each day a person is actively managing their e-mails indicates a greater level of stress. A data collection module operating on the user's electronic devices collects data concerning the users total e-mail usage.

The data collection module may also collect data concerning a user's phone usage. For example, the data collection module operating on the user's mobile electronic device 102 may collect data indicative of number of phone calls made, the duration of phone calls, and the times that the phone calls are made. The more phone calls that a user makes, the longer the phone calls, and the greater the amount of time that a person is actively making phone calls indicates a greater level of stress. In addition, the data collection module may collect data concerning the tone of voice and other voice pattern data of the user during the phone calls. Accordingly, the data collection module may collect data from the mobile electronic device's microphone to analyze the user's voice. The voice data may be used to determine if the person is yelling, speaking with a happy tone, angry tone, excitedly, with a depressed tone, or other emotional states. For example, if the person in speaking loudly and the voice data indicates that the person is angry, this data is indicative of a higher level of stress. For example, conventional voice analysis programs may determine a person's emotional state based on speech patterns.

The data collection module collects appointment information that may be stored and managed by appointment management programs operating on the user's electronic devices. For example, many e-mail programs include calendars that allow users to store dates, times, and locations for meetings. Other appointment management programs may also be running on the user's electronic devices from which the data collection module collects appointment data. The data collection module collects the user's appointment data. The greater the number of appointments, the longer the appointments, the greater the proximity in time of each appointment, and the greater the distance to travel to each appointment are indicative of a higher level of stress.

Preferably, the mobile electronic device 102 includes a positioning device 112 that is capable of determining the location of the device using GPS, cell tower triangulation, or other location means. The data collection module periodically collects position information from the positioning module that represents the current location of the user as the user carries the mobile electronic device throughout the day. The location data may be used to determine the amount of time a user is in the office, traveling, at appointments or other meetings, etc. The greater the amount of time the user spends in the office, traveling, and at appointments or meetings is indicative of a greater level of stress.

A noise monitoring module executing on a processor of the mobile electronic device 102 may send instructions to the processor to activate the microphone. The data collection module collects data from the microphone indicative of the volume of the ambient noise that is detected by the microphone. A person that is exposed to high volume noise throughout the day is likely to experience greater levels of stress. Accordingly, a greater level of ambient noise that the user is exposed to and a longer duration of the noise are indicative of a higher level of stress in a user.

The mobile electronic device 102 may also include a weather monitoring module that may collect weather information at a user's location from the internet. The data collection module collects weather related information such as temperature, humidity, and perception conditions. Extremes in temperature (hot or cold), high humidity, and rain or snow conditions may increase the amount of stress experienced by a user.

The e-mail usage data, phone usage data, appointment data, location data, voice data, ambient noise data, weather data, and other parameters that are collected by the data collection module are reported by a reporting module. The reporting module communicates the data collected by the data collection module to a listening module. The listening module may be a program executing on the processor of the user's mobile electronic device 102 or it may be a module executing on a remote server 104 connected to the internet. The listening module receives the data provided by the reporting module. The listening module communicates the data to a computing module that transforms the data into a stress-score. The stress-score may be a numerical value that indicates the stress experienced by a user as a result of their activities and stimuli.

Factors contributing to chronic stress can be estimated from various sources, including, for example, self-assessment questionnaires, biochemical clinical measures, and heart rate variability measures. Heart rate variability (HRV) provides a useful indicator to estimate a level of chronic stress in an individual. In accordance with the factors, the stress-score may be calculated based on the level of e-mail usage, telephone usage, user voice characteristics, user appointments, user location and travel data, and the user's ambient conditions such as noise and weather. Available information includes, but it is not limited to: heart R-R intervals; anthropomorphic data; Cortisol level; Dehydroepiandrosterone ("DHEA") levels and voice spectral decomposition. Heart R-R intervals, questionnaires, and voice spectral decomposition may be measured, obtained and/or performed via a mobile computing device such as a smartphone and in connection with one or more respective sensor devices. Other factors, such as Cortisol and DHEA levels, may not be obtained via a standard mobile device, given that these may be tests that include blood or other physical samples. Alternatively, such factors may be obtained with a suitably configured device that includes, for example, "lab-on-a-chip" technology, as known in the art.

Information that may be derived includes, but is not limited to: resting heart rate; heart rate time series; dispersion metrics of HEW; time domain characteristics of HRV; frequency domain characteristics of HRV; estimates of relative parasympathetic tone; and estimates of relative sympathetic tone.

In an implementation, one or more protocols may be used in the determination and/or calculation of the stress-score. One non-limiting example protocol includes:
 one or two measurement series of Cortisol and DHEA (e.g., four saliva samples over a 24-hours period, each a obtained a minimum of two hours after a meal);
 execution of self-assessment (e.g., Maslach Burnout Inventory, Cohen's stress instrument) (these are periodic, low periodicity, e.g., once every 2-3 months);
 electrocardiographic recording, single channel, at rest, 20 minutes (this is repeated periodically, with moderate periodicity, e.g., once a month), which may be obtained via a Wahoo chest strat or similar device;
 direct and derived information, such as identified above, is used to build predictive inductive models using accepted chronic stress measures and anthropomorphic and biometric user-data as dependent variables;
 a best predictor and minimal set of independent predictor variables are chosen;
 a model or potentially several models may be recalibrated, as new data are collected from users; and
 a single final measure of stress is derived from model output(s).

With regard to usage, given the model or models derived using the above protocol, and given the selected predictive input variables, the latter are input automatically or manually into a tracker device (e.g., mobile computing device such as an IPHONE, DROID or other smartphone), which uses the derived models to produce a measure of chronic stress as output.

As discussed above, the greater a user's e-mail usage, the greater a user's telephone usage, the greater the stress indicators in a user's voice (e.g. volume and other stress patterns), the more demanding a user's appointment schedule, the more time a user spends at work and traveling, the louder the ambient noise and the more extreme the ambient weather conditions, the greater the user stress level and stress-score will be. Accordingly, the computing module transforms all the available data into a score that indicates the user's stress level.

In one or more implementations, a use of the stress-score that is calculated in accordance with the teachings herein may be, for example, to cause one or more messages to be generated and/or delivered substantially automatically that informs or advises the sender that the recipient is currently "out of the office," "temporarily unavailable" or the like in order to reduce stress for the recipient, or which changes the alert state of the user's device to change the number of alerts actually provided to the user as compared to the number of messages received. Moreover, an implementation may be provided that assists to prioritize telephone calls, e-mail messages, text messages, or the like, and further may suppress those calls and/or messages that are deemed to be non-urgent.

In an implementation, messages may be determined to be of greater or lesser urgency in accordance with an individual's calculated stress-score. For example, a determination may be made for an individual who has been determined to have a particularly high stress-score, that many messages (e.g., text messages, e-mail messages and/or telephone messages) are to be classified as non-urgent. As a consequence, the sending party can be notified that the recipient is temporarily unavailable or the individual will receive only receive alerts for messages that are not classified as non-urgent. Alternatively, many messages that are sent to an individual who has been determined to have a low stress-score may not be blocked or otherwise managed. Thus, in one implementation, a form of message management with substantially automatic notifications may be provided in accordance with an individual's stress-score, and the same or another form of message management can alter the number of alerts relative to the number of messages received.

Further, rules may be defined by an individual that sets priorities for messages that are sent to the individual and that should be handled automatically, such as to inform a sending party that the individual is unavailable. For example, an e-mail message is sent to an individual having a relatively high stress-score and who has defined rules for handling e-mail messages. The rules may regard senders of e-mails, subject lines of e-mails or other criteria associated with messages. Based on the rules and the relatively high stress-score, a reply to the message is automatically generated and transmitted to inform the sending party that the individual is unavailable. Thus, mechanisms are provided that manage messages for individuals and that assist to prevent additional stress from being incurred as a result of additional messaging.

Figure 2:
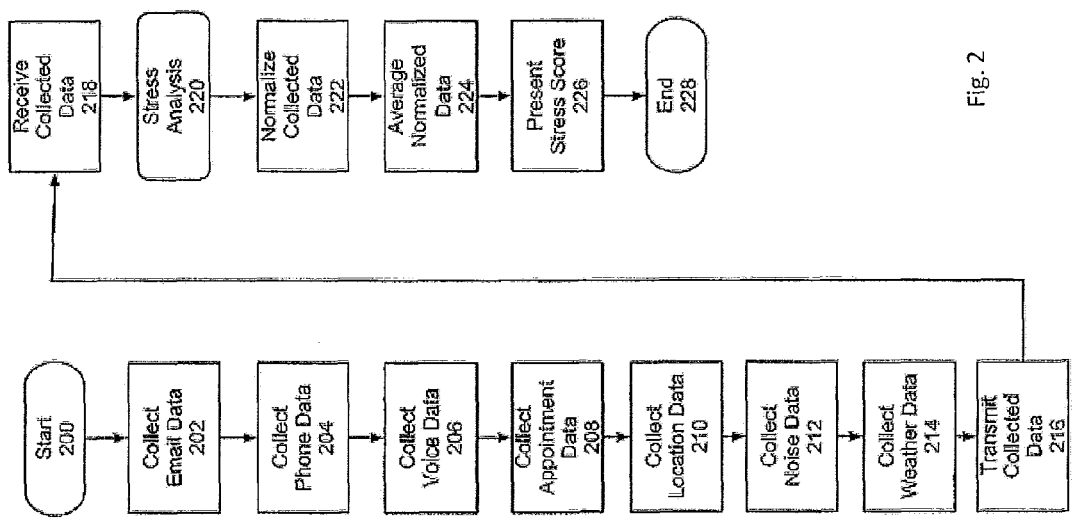
FIG. 2 is a flowchart illustrating a process of calculating a stress-score.

Referring now to FIG. 2, system is initiated at step 200. The data collection module collects e-mail usage data at step 202, phone data at step 204, voice data at step 206, appointment data at step 208, location data at step 210, noise data at step 212, and weather data at step 214. These steps may be performed in any order and may be performed multiple times throughout a given day or set time period. For example, the noise collection step 212 may be set to be performed a set number of times through the day (e.g., every hour). Other collection steps may be performed as events occur. For example, the e-mail data collection step 202 may be performed every time the user sends, receives, or views an e-mail. Accordingly, the order of the steps is illustrative, and may be repeated and/or reorder as necessary.

The collected data may be transmitted by the reporting module at step 216 and received by the listening module at step 218. The listing module provides the data to the computing module at step 220 for stress analysis. In at least one implementation in which the data collection module and the computing module are executing on the same device (e.g., a mobile electronic device), the computing module may access the data from the data collection module.

At step 222, the collected data for each parameter is normalized. For example, e-mail volume may be normalized to a score between 0 and 1000. Zero e-mails received in a day may be equal to a score of zero and 500 or more e-mails a day may be equal to a score of 1000, and a number between zero and 500 e-mails is equal to a scaled score between 0 and 1000. This is just an example of how the data may be normalized. At step 222 all the collected data may be normalized by setting upper and lower bounds and assigning a score depending on where the collected data values falls between the upper and lower bounds.

At step 224, the normalized values for each of the collected parameters are averaged. The averaged normalized values represent the user's stress-score. At step 226, the stress-score is present to the user. At step 228, the process ends.

In at least one implementation, the stress-score may then be transmitted to a person of authority at the user's workplace (e.g., human resources personnel). If the score is too high, human resources may instruct supervisors or the user to try to reduce the stress-score by reducing stress factors (such as appointments or travel). The computing module of the system 100 may also analyze the data for factors that are contributing to a high level of stress and make recommendations to the user to reduce stress (e.g., set a cut off time for answering e-mails) Accordingly, the system provides a means of actively monitoring a user's stress levels and providing recommendations to reduce stress. In this way, the risk of burn out of an employee due to stress may be reduced.

In at least one other implementation, data collection and reporting modules may be placed onto other electronic devices of the user, such as the user's home computer, work computer, laptop, tablet, or other electronic devices. Accordingly, more data about a user's stress factors (e.g., e-mail usage, etc.) based on activities performed on other electronic devices may be gathered to provide additional accuracy of the user's stress-score. The reporting modules on each of the user's electronic devices may report the collected data to the remote server 104. A computing module operating on the processor of the remote server may transform the data into a stress-score. The stress-score may then be communicated back to the electronic devices so that the user may view the score and/or the user may log onto the remote server via a web interface over the internet to review the stress-score data.

The stress-score may also be used as a component in calculating a user's overall health score, as described in co-pending U.S. Provisional Patent Application, Ser. No. 61/495,247, filed Jun. 9, 2011, titled Health Data Acquisition, Processing and Communication System, which is hereby incorporated by reference in its entirety. A user with a high stress-score will cause the user's overall health score to go down.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

The various embodiments described above disclose features that can optionally be combined in a variety of ways depending on the desired implementation. It will be appreciated that other embodiments based on different combinations of features are also possible. For example, collection may be performed for only some of the data types illustrated in FIG. 2 or other data types may also be collected and taken into account in determining the stress score.

It will also be appreciated that more than one parameter for a particular parameter type may be used. For example, a first parameter on the amount of email received and a second parameter on amount of email viewed may be obtained and used in calculating an individual's stress score. As an alternative to having multiple parameter from a particular parameter type, a single composite parameter for each type may be determined such that a parameter for email related data may be determined, another for telephone correspondence etc.

None of the described features are mutually exclusive, and any combination of may be deployed to achieve the functions described above.

We claim:

1. A computer implemented method for analyzing an individual's personal stress level and providing a stress-score representing the individual's personal stress level, comprising the steps of:
    receiving, into a memory from at least one computing device, parameter data representing a plurality of parameters, each of the parameters respectively representing a factor of the individual's life that contributes to a level of stress for the individual, wherein the plurality of parameters include at least two selected from a group consisting of: an e-mail correspondence parameter, a telephone correspondence parameter, a travel parameter, a task parameter, an appointment parameter, a meeting parameter, a time at work parameter, an ambient noise parameter, a weather parameter, a sleeping habits parameter, an eating habits parameter and a health-related information parameter;
    processing the received parameter data by executing code in a processor that configures the processor to normalize the parameter data by assigning, for each of the received parameters, a respective parameter score that represents a relative value of the parameter;
    calculating the individual's stress-score as a function of the normalized parameter data; and
    automatically transmitting the stress-score to the at least one computing device, using code executing in the processor and free of human intervention.

2. The method of claim 1, wherein normalizing the parameters comprises executing code in the processor that configures the processor to determine, for each of the received parameters, an upper bound parameter value and a lower bound parameter value.

3. The method of claim 2, further comprising executing code in the processor that configures the processor to normalize the parameter data by assigning, for each of the received parameters, a respective parameter score that is within the respective parameter's upper bound parameter value and the lower bound parameter value.

4. The method of claim 3, wherein calculating the individual's stress-score includes averaging the normalized parameter data.

5. The method of claim 1, wherein the e-mail correspondence parameter represents at least one selected from a group consisting of: amount of e-mail received, amount of e-mail viewed, amount e-mail sent, length of an e-mail message, amount of time spent working with e-mail, and time of day working with e-mail.

6. The method of claim 1, wherein the telephone correspondence parameter represents at least one selected from a group consisting of: number of telephone calls made, number of telephone calls received, duration of a telephone call, time of day of a telephone call, individual's tone of voice during a telephone call, and individual's voice pattern during a telephone call.

7. The method of claim 1, wherein the travel parameter represents at least one selected from a group consisting of: location, time of year, and amount of travel.

8. The method of claim 1, wherein the tasks parameter represents at least one selected from a group consisting of: type of task, quantity of tasks, and time of day for performing a task.

9. The method of claim 1, wherein the appointments parameter represents at least one selected from a group consisting of: type of appointment, quantity of appointments, and time of day for an appointment.

10. The method of claim 1, wherein the meeting parameter represents at least one selected from a group consisting of: type of meeting, count of meetings, and time of day for a meeting.

11. The method of claim 1, wherein at least one of the travel parameter, task parameter, appointment parameter and the meeting parameter are determined as a function of Global Positioning System technology.

12. The method of claim 1, wherein at least one of the e-mail correspondence parameter, the telephone correspondence parameter, the travel parameter, the task parameter, the appointment parameter, the meeting parameter, the time at work parameter, the ambient noise parameter, and the weather parameter is obtained as a function of a software application executed on the at least one computing device.

13. The method of claim 1, further comprising executing code in the processor that configures the processor to generate a report that includes the stress-score.

14. The method of claim 1, further comprising executing code in the processor that configures the processor to generate and transmit a message to at least one other computing device, wherein the message is generated and transmitted based on at least the stress-score.

15. The method of claim 14, wherein the message informs the respective user of the at least one other computing device that the individual is temporarily unavailable.

16. The method of claim 14, wherein the message is further generated as a function of at least one rule defined by the individual.

17. The method of claim 14, wherein the at least one rule relates to at least one of a sender of an e-mail and a subject line of an e-mail message.

18. The method of claim 1, further comprising executing code in the processor that configures the processor to receive information associated with at least one protocol used in the determination of the stress-score.

19. A computer implemented stress-score calculating system comprising:
    a communication unit operable to receive, from at least one computing device, parameter data representing a plurality of parameters, each of the parameters respectively representing a factor of the individual's life that contributes to a level of stress for an individual, wherein the plurality of parameters include at least two selected from a group consisting of: an e-mail correspondence parameter, a telephone correspondence parameter, a travel parameter, a task parameter, an appointment parameter, a meeting parameter, a time at work parameter, an ambient noise parameter, a weather parameter, a sleeping habits parameter, an eating habits parameter and a health-related information parameter;
    a memory arranged to store the received parameter data;
    a processor arranged to process the received parameter data by executing code that configures the processor to normalize the parameter data by assigning, for each of the received parameters, a respective parameter score that represents a relative value of the parameter;

the processor being further arranged to execute code to:
calculate the individual's stress-score as a function of the normalized parameter data; and
automatically transmit the stress-score to the at least one computing device.

20. The system of claim 19, wherein the processor is further arranged to normalize the parameters by executing code in the processor that configures the processor to determine, for each of the received parameters, an upper bound parameter value and a lower bound parameter value.

21. The system of claim 20, wherein the processor is further arranged to assign, for each of the received parameters, a respective parameter score that is within the respective parameter's upper bound parameter value and lower bound parameter value.

22. The system of claim 20, wherein the processor is further arranged to calculate the individual's stress-score by averaging the normalized parameter data.

23. The system of claim 19, wherein the e-mail correspondence parameter represents at least one selected from a group consisting of: amount of e-mail received, amount of e-mail viewed, amount e-mail sent, length of an e-mail message, amount of time spent working with e-mail, and time of day working with e-mail.

24. The system of claim 19, wherein the telephone correspondence parameter represents at least one selected from a group consisting of: number of telephone calls made, number of telephone calls received, duration of a telephone call, time of day of a telephone call, individual's tone of voice during a telephone call, and individual's voice pattern during a telephone call.

25. The system of claim 19, wherein the travel parameter represents at least one selected from a group consisting of: location, time of year, and amount of travel.

26. The system of claim 19, wherein the tasks parameter represents at least one selected from a group consisting of: type of task, quantity of tasks, and time of day for performing a task.

27. The system of claim 19, wherein the appointments parameter represents at least one selected from a group consisting of: type of appointment, quantity of appointments, and time of day for an appointment.

28. The system of claim 19, wherein the meeting parameter represents at least one selected from a group consisting of type of meeting, count of meetings, and time of day for a meeting.

29. The system of claim 19, wherein at least one of the travel parameter, task parameter, appointment parameter and the meeting parameter are determined as a function of Global Positioning System technology.

30. The system of claim 19, wherein at least one of the e-mail correspondence parameter, the telephone correspondence parameter, the travel parameter, the task parameter, the appointment parameter, the meeting parameter, the time at work parameter, the ambient noise parameter, and the weather parameter is obtained as a function of a software application executed on the at least one computing device.

31. The system of claim 19, wherein the processor is further arranged to execute code that configures the processor to generate a report that includes the stress-score.

32. The system of claim 19, wherein the processor is further arranged to execute code that configures the processor to generate and transmit a message to at least one other computing device, wherein the message is generated and transmitted based on at least the stress-score.

33. The system of claim 32, wherein the message informs the respective user of the at least one other computing device that the individual is temporarily unavailable.

34. The system of claim 32, wherein the message is further generated as a function of at least one rule defined by the individual.

35. The system of claim 32, wherein the at least one rule relates to at least one of a sender of an e-mail and a subject line of an e-mail message.

36. The system of claim 19, wherein the processor is further arranged to execute code that configures the processor to receive information associated with at least one protocol used in the determination of the stress-score.

37. A computer implemented method for collecting information associated with an individual's personal stress level and receiving a stress-score representing the individual's personal stress level, comprising the steps of:

obtaining parameter data representing a plurality of parameters, each of the parameters respectively representing a factor of the individual's life that contributes to a level of stress for the individual, wherein the plurality of parameters include at least two selected from a group consisting of: an e-mail correspondence parameter, a telephone correspondence parameter, a travel parameter, a task parameter, an appointment parameter, a meeting parameter, a time at work parameter, an ambient noise parameter, a weather parameter, a sleeping habits parameter, an eating habits parameter and a health-related information parameter;

transmitting the parameter data to at least one computing device; and receiving, from the at least one computing device, the stress-score.

38. A computer implemented system for collecting information associated with an individual's personal stress level and receiving a stress-score representing the individual's personal stress level, comprising the steps of:

a communication unit operable to receive parameter data representing a plurality of parameters, each of the parameters respectively representing a factor of the individual's life that contributes to a level of stress for an individual, wherein the plurality of parameters include at least two selected from a group consisting of: an e-mail correspondence parameter, a telephone correspondence parameter, a travel parameter, a task parameter, an appointment parameter, a meeting parameter, a time at work parameter, an ambient noise parameter, a weather parameter, a sleeping habits parameter, an eating habits parameter and a health-related information parameter;

a memory arranged to store the received parameter data;

wherein the communication unit is further configured to transmit the parameter data to at least one computing device and to receive, from the at least one computing device, the stress-score.

\* \* \* \* \*